United States Patent

(12) United States Patent
Eriksson

(10) Patent No.: US 9,387,416 B2
(45) Date of Patent: Jul. 12, 2016

(54) METHOD AND ARRANGEMENT FOR SECURING A DISTRIBUTOR PLATE TO A BACKING PLATE OF A CHROMATOGRAPHY COLUMN

(75) Inventor: Stefan K. Eriksson, Uppsala (SE)

(73) Assignee: GE Healthcare BioSciences AB, Uppsala (SE)

( * ) Notice: Subject to any disclaimer, the term of this patent is extended or adjusted under 35 U.S.C. 154(b) by 231 days.

(21) Appl. No.: 13/990,155

(22) PCT Filed: Nov. 16, 2011

(86) PCT No.: PCT/SE2011/051380
§ 371 (c)(1),
(2), (4) Date: May 29, 2013

(87) PCT Pub. No.: WO2012/074455
PCT Pub. Date: Jun. 7, 2012

(65) Prior Publication Data
US 2013/0248431 A1 Sep. 26, 2013

(30) Foreign Application Priority Data
Nov. 29, 2010 (GB) .................................. 1020148.1

(51) Int. Cl.
B01D 15/22 (2006.01)
G01N 30/60 (2006.01)
B01D 15/14 (2006.01)

(52) U.S. Cl.
CPC ............ *B01D 15/22* (2013.01); *G01N 30/6004* (2013.01); *G01N 30/6017* (2013.01); *G01N 30/6021* (2013.01); *Y10T 29/49826* (2015.01)

(58) Field of Classification Search
None
See application file for complete search history.

(56) References Cited

U.S. PATENT DOCUMENTS

| 3,210,577 | A | * | 10/1965 | Hogue ............................. 310/43 |
| 5,141,635 | A | * | 8/1992 | LePlang et al. ............. 210/198.2 |
| 5,603,899 | A | * | 2/1997 | Franciskovich et al. ...... 422/527 |
| 5,753,795 | A | * | 5/1998 | Kuypers ........................ 73/23.37 |
| 6,352,266 | B1 | | 3/2002 | Rigoli |
| 7,553,455 | B1 | * | 6/2009 | Renzi et al. .................... 422/546 |
| 7,780,853 | B2 | | 8/2010 | Davis et al. |
| 8,287,737 | B2 | * | 10/2012 | Bielawski et al. ............. 210/656 |
| 2004/0182789 | A1 | * | 9/2004 | Gill et al. ....................... 210/656 |
| 2010/0230340 | A1 | * | 9/2010 | Bielawski et al. .......... 210/198.2 |
| 2013/0240426 | A1 | | 9/2013 | Ramakrishna |

FOREIGN PATENT DOCUMENTS

| WO | WO 96/26436 | 8/1996 |
| WO | WO 2009/041877 | 4/2009 |
| WO | WO 2009/093952 | 7/2009 |
| WO | WO 2010/132011 | 11/2010 |

* cited by examiner

Primary Examiner — Katherine Zalasky
Assistant Examiner — Kara Graber
(74) Attorney, Agent, or Firm — Wood IP LLC

(57) ABSTRACT

A chromatographic column that includes a distributor plate secured to a backing plate of the chromatography column without the need for releasable fixing means such as screws or bolts, by employing a negative pressure or vacuum to affix the distributor to the backing plate.

5 Claims, 3 Drawing Sheets

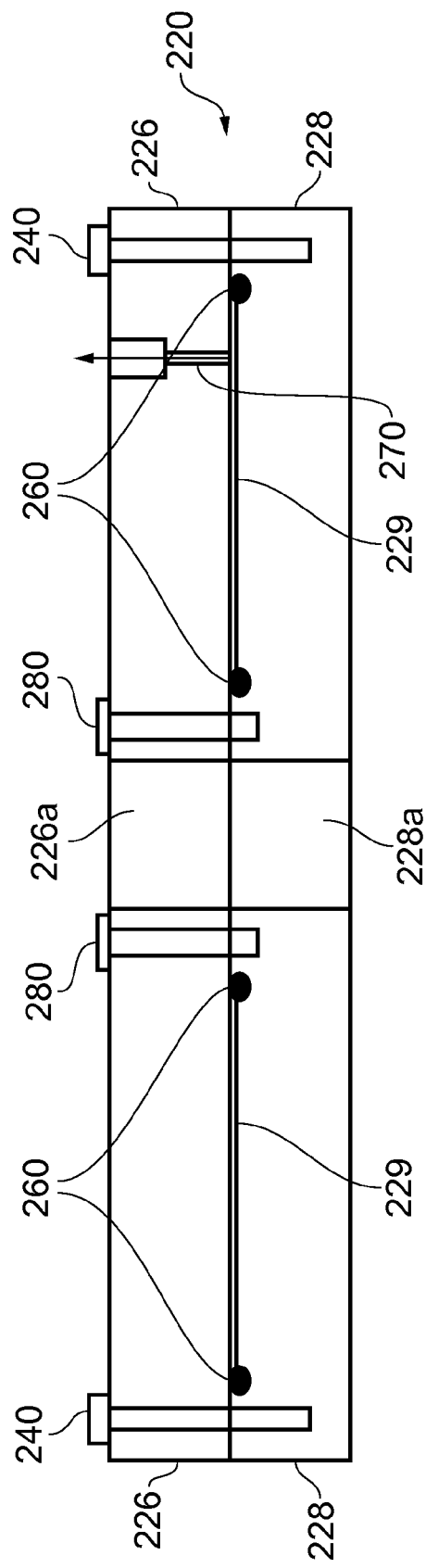

METHOD AND ARRANGEMENT FOR SECURING A DISTRIBUTOR PLATE TO A BACKING PLATE OF A CHROMATOGRAPHY COLUMN

CROSS-REFERENCE TO RELATED APPLICATIONS

This application is a filing under 35 U.S.C. 371 of international application number PCT/SE2011/051380, filed Nov. 16, 2011, published on Jun. 7, 2012 as WO 2012/074455, which claims priority to patent application number 1020148.1 filed in Great Britain on Nov. 29, 2010.

TECHNICAL FIELD

The present invention relates to chromatography columns and their component parts. In particular, the present invention relates to methods for securing a distributor plate to a backing plate of a chromatography column.

BACKGROUND TO THE INVENTION

Chromatography columns may be used in industrial processes to purify process liquids and separate substances of interest from process liquids; typical examples include large-scale preparative purification of fine chemicals and pharmaceuticals, together with biological products. Industrial-scale chromatography columns typically comprise a hollow, axially vertical tubular housing or tube including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor which further supports a bed support: a bed support is a layer of mesh, filter, sinter, screen or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement which allows clearance for outlet pipe work projecting beneath the base assembly.

Prior art adapter and base assemblies are formed by screwing or bolting the distributor plate into the backing plate by means of bolts or screws. As the distributor is made of inert non metallic materials, such as plastic, it may become distorted during the operation of the column when it is subjected to internal pressures ranging from −1 bar to +5 bar. To overcome this problem, the distributor is secured to the backing plate with many screws or bolts. This process typically requires helicoil threads being cut into the backing plate, a process that can be costly and difficult to implement in high quality materials like stainless steel and other materials which are suitable for use in a GMP environment, and securing the distributor to the backing plate using appropriately threaded screws or bolts.

A significant number of such bolts or screws are required (e.g. in 1 meter diameter column there would typically 20 to 40 screws or bolts and for a 2 meter diameter column approximately 100 to 150 screws or bolts) to secure the distributor to the backing plate as the resulting assembly must be able to withstand back compression pressures when, for instance, the column is being packed.

The process of securing the distributor plate to the backing plate by the use of screws and/or bolts can be time consuming when the chromatography column is initially being set up for operation. Errors may occur in the set up process when screws or bolts of the wrong length or incorrect bore are used, resulting in a weaker seal between the component parts.

Corrosion of the screws or bolts, and of the screw threads, can occur with time and repeated use of the column. Furthermore, the cleaning and/or maintenance of the column often necessitates the separation of the distributor plate from the backing plate. Once again, this process requires time to carefully unscrew or unbolt the distributor from the backing plate.

There is therefore a need for chromatography columns which have a simpler, cost-effective means of securing the distributor plate to the backing plate to overcome the above mentioned problems encountered in the prior art.

SUMMARY OF THE INVENTION

In a first aspect of the present invention, there is provide a method of securing a distributor plate to a backing plate of a chromatography column comprising the steps of:
  a) providing a chromatography column comprising:
    a liquid inlet and a liquid outlet;
    a tube in contact with an adapter assembly and a base assembly to define a cavity therebetween,
    said adapter assembly and said base assembly each comprising a backing plate and a distributor plate;
    sealing means between said backing plate and said distributor plate of the adapter assembly and/or between the backing plate and the distributor of the base assembly, said sealing means defining an air pocket therebetween;
    the backing plate of the adapter assembly and/or the backing plate of the base assembly having a passage in fluid connection with said air pocket and a vacuum pump; and
  b) removing the air from the air pocket via said passage with said vacuum pump to secure the distributor plate to the backing plate.

In one aspect, the vacuum pump is not an integral part of the column, thus providing more flexibility for its use. For example, the vacuum pump may be a separate entity to the column or a component part of a separate device such as a packing station for packing chromatography columns.

In another aspect, both backing plates have a passage in fluid connection with an air pocket and the vacuum pump. In this embodiment, the distributor plate of both the adapter assembly and the base assembly would be secured to each other by means of a vacuum.

In a further aspect, the sealing means is one or more O-rings. Other forms of sealing means which could be used to define an air pocket are possible. The sealing means are made from an inert, compressible material such as plastic, silicone or rubber (EPDM seals being preferable). The shape of the sealing means can vary, for example they may be circular, square, rectangular or oblong in shape. A circular or O ring shape is preferable.

In one aspect, locating means can be used to co-locate the backing plate and the distributor plate. Examples of locating means include but are not limited to pins or studs which fit into corresponding holes or notches.

In another aspect, the air pocket can be filled with air to thereby release the distributor plate from the backing plate.

In a second aspect of the present invention, there is provided a chromatography column comprising:
 a) a liquid inlet and a liquid outlet;
 b) a tube connected to an adapter assembly and a base assembly to define a cavity therebetween, said adapter assembly and said base assembly each comprising a backing plate and a distributor plate;
 c) sealing means between said backing plate and said distributor plate of the adapter assembly and/or between the backing plate and the distributor of the base assembly, said sealing means defining an air pocket therebetween;
 d) the backing plate of the adapter assembly and/or the backing plage of the base assembly having a passage in fluid connection with said air pocket; and
 e) a vacuum pump In one aspect, the vacuum pump is not an integral part of the column. For example, the vacuum pump may be a separate entity to the column or a component part of a separate device such as a packing station for packing chromatography columns.

In another aspect, both backing plates have a passage in fluid connection with an air pocket and the vacuum pump. In this embodiment, the distributor plate of both the adapter assembly and the base assembly would be secured to each other by means of a vacuum.

In a further aspect, the sealing means is one or more O-rings. Other forms of sealing means which could be used to define an air pocket are possible. The sealing means are made from an inert, compressible material such as plastic, silicone or rubber (EPDM seals being preferable). The shape of the sealing means can vary, for example they may be circular, square, rectangular or oblong in shape. A circular or O ring shape is preferable.

In one aspect, locating means can be used to co-locate the backing plate and the distributor plate. Examples of locating means include but are not limited to pins or studs which fit into corresponding holes or notches.

BRIEF DESCRIPTION OF THE DRAWINGS

The features and advantages of the invention will become apparent from the following description taken in connection with the accompanying drawings in which:

FIG. 2 is a schematic sectional front view of an assembly of chromatography column in accordance with the invention.

DETAILED DESCRIPTION OF THE INVENTION

Figure 1:
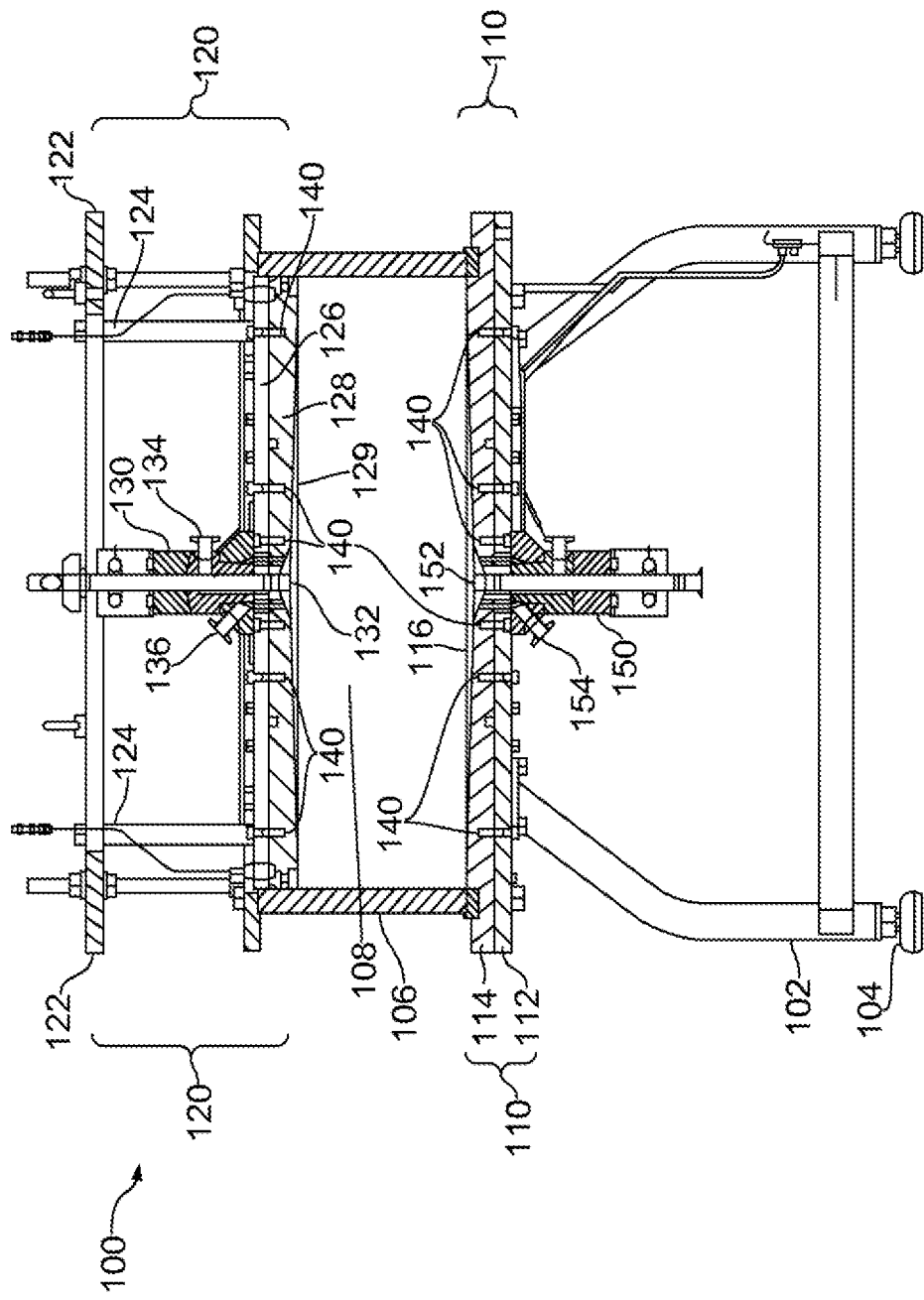
FIG. 1 shows a sectional front view of a chromatography column known in the art in which the distributor plate is secured to the backing plate by screws.

FIG. 1 is a sectional front view of a chromatography column 100 known in the art. The column 100 is made of strong, inert materials such as stainless steel and other materials which are suitable for use in a GMP environment typical of the pharmaceutical industry. The column 100 is supported on legs 102 having feet 104 which are adjustable in order to modify the height and/or the level of the column. The legs 102 support the column 100 which comprises a cylindrical housing or tube 106 defining a cavity 108, for receipt of chromatographic media, separating a base assembly 110 at one end from an adapter assembly 120 at the other. The tube 106 may typically be made from stainless steel, or other strong, inert materials. Adjacent to the adapter assembly 120 is a dispersion system 130 comprising a nozzle 132 which includes a mobile phase pathway 134, for the introduction of buffer or other suitable mobile phase liquids or chemicals/materials to be separated, and a liquid inlet 136. The adapter assembly 120 may be moveable within the cavity 108 of the tube 106 in an operational mode, for example, to pack or compress the bed of chromatographic media used to effect chromatographic separation of chemicals within the column. In the figure, the adapter assembly 120 comprises an adapter flange 122, one or more distance pillars 124, a backing plate 126 made typically of stainless steel, a distributor 128 made from inert, non-metallic material which may take the form of a plate having many channels to effect the even distribution of liquids, and a bed support 129 comprising a screen or mesh or filter and optionally a sealing ring (not shown). The bed support 129 may be made of an inert plastic or metal material such as stainless steel. The distributor 128 and bed support 129 are fastened to each other by releasable fixing means (not shown). Typical releasable fixing means 140 which secure the distributor 128 to the backing plate 126 include, but are not limited to, screws and bolts. Generally, the fixing means is a screw which is inserted through a threaded hole in the backing plate 126 into the distributor 128.

The fixing means 140 may be accessed and thus released from the exterior face of the distributor 128 or backing plate 126, that is the face of the plate furthest away from the cavity 108. Access may be gained from the exterior face of the backing plate or distributor to avoid unnecessary exposure of the operator to a suspended or supported load within the column.

The base assembly 110 comprises a backing plate 112 and a distributor 114, fastened to each other by releasable fixing means 140, and a bed support 116. The backing plate 112 is made typically of stainless steel while the distributor 114 may take the form of a plate having many channels to effect the even distribution of liquids. The bed support 116 comprises a screen or mesh or filter and optionally a sealing ring (not shown) and is attached to the distributor 114 by releasable fixing means (not shown). The bed support 116 may be made of an inert plastic or metal material such as stainless steel. The fixing means 140 can take the form of a screw or bolt inserted through corresponding holes around the perimeter of the components; typically the fixing means is a screw which is inserted through a hole in the backing plate 112 into a threaded aperture in the distributor 114. In the example shown, access is obtained from the exterior face of the backing plate 112 to avoid operator exposure beneath a suspended load, It will be understood that separation of chemical or biological materials on the column, when the tube 106 is full of chromatographic media, can be carried out in either a downward or upward flow. Thus, in a downward flow, liquid containing chemical or biological materials to be separated is introduced through nozzle 132 and moves in a downward direction through the bed of media, to be collected in the collection system at the base of the column through nozzle 152 of dispersion system 150 via an outlet port 154. In upward flow mode, liquid containing materials to be separated is introduced via the bottom nozzle 152 and flows upwards through the media bed to be collected at the top of the column via nozzle 132 and inlet 136.

FIG. 2 shows a schematic, front sectional view of an assembly of a chromatographic column in accordance with the invention. The assembly in the figure is an example of an adapter assembly but it will be understood by the skilled person that the same principle of operation would equally apply to a base assembly. Moreover, it will be further understood that a chromatography column in accordance with the present invention may comprise both an adapter assembly and base assembly.

The adapter assembly 220 comprising a backing plate 226 and a distributor plate 228. The backing plate 226 and distributor plate 228 have a circular configuration with a central hole therein (226a and 228a) for each of alignment and location around the liquid inlet/outlet (not shown). The backing plate and the distributor plate can be co-located using a locating means including but not limited to pins or studs 280 which fit into corresponding holes or notches. Further, a small number of screws 240 are present which hold the distributor 228 to the backing plate 226 in a resting position and also serve to compress the sealing means or O ring 260 to create an air pocket 229 between the backing plate 226 and the distributor 228. In a different embodiment (not shown) these screws can also be utilized to secure a bed support to the distributor plate.

An air pocket 229 is formed between the backing plate 226 and the distributor plate 228 by sealing means 260. The size of the air pocket may be governed by the size/dimensions of the sealing means and/or the configuration of the contacting surfaces of the backing plate 226 and the distributor plate 228. For example, a section of one or both contacting surfaces of the backing plate 226 and/or distributor plate 228 may be recessed or inlaid to create a larger air pocket 229, as defined by sealing means 260, when the two surfaces come into contact. The sealing means 260 is made of an inert, compressible material such as plastic, silicone or rubber (EPDM seals being preferable), and may take the form of a ring, such as an O ring. The sealing means 260 forms an airtight seal to create air pocket 229. Air is removed from the air pocket 229 via passage 270 by a vacuum pump exerting a negative pressure of typically 0.1 to 1.0 bar. The vacuum pump may be an integral part of the chromatography column or may be separate to the column, for example part of a packing station which is used to pack the column with chromatographic media.

Figure 3B:
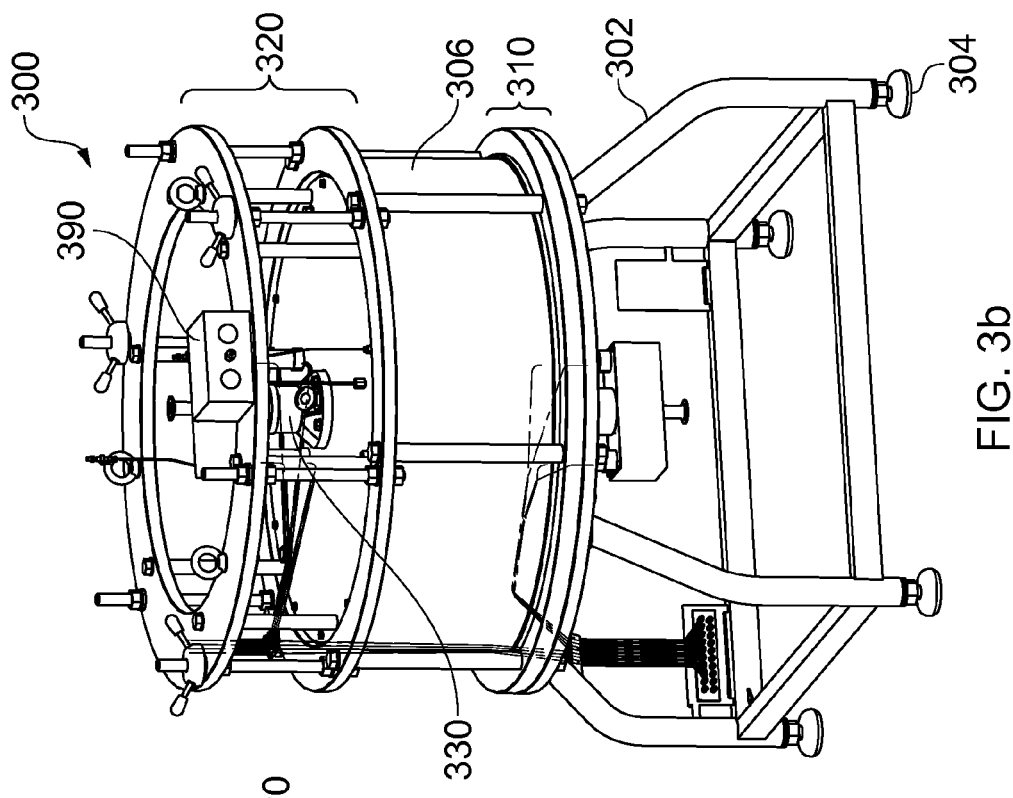
FIG. 3b is a front perspective view of the column shown in FIG. 3a but without the partial, sectional view.
Figure 3A:
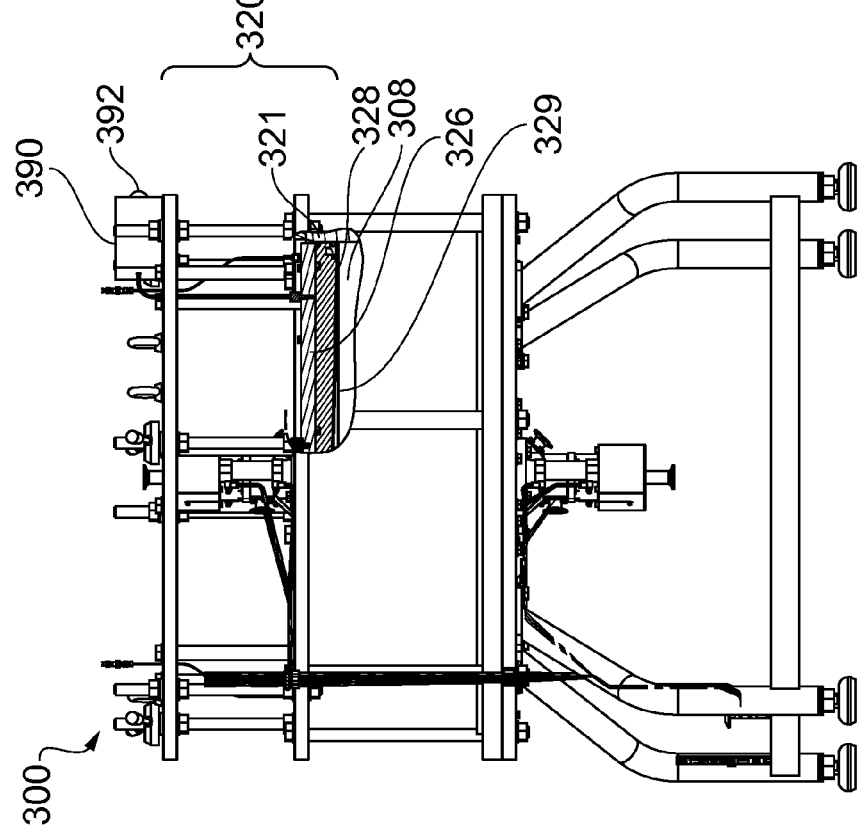
FIG. 3a is side perspective view of a column and a partial sectional view of an adapter assembly according to embodiments of the present invention.

FIG. 3a is a side view of a column 300 according to the invention with a partial cut away or sectional view 321 of an adapter assembly 320 showing the internal arrangement of the backing plate 326, distributor plate 328 and bed support 329. The distributor plate 328 is secured to the backing plate 326 by means of a vacuum which is applied from a vacuum pump (not shown) which is external to the column 300. The vacuum pump may be an integral part of the column or it may be a separate entity or part of another device (e.g. a packing station for packing the column with chromatographic media). Although not shown in the figure, an air pocket is created by sealing means, such as an O-ring, between the contacting surfaces of the backing plate 326 and distributor plate 328. Air can be removed via a passage (not shown) in the backing plate 326 by application of a negative pressure. In operation, a vacuum of 0.1 to 1 bar is applied by a pump to remove air from the chamber and secure the distributor plate 328 to the backing plate 326. Optionally, a base assembly (not shown) may be present in the column 300 which utilizes a vacuum to secure the backing plate to the distributor.

A control box (390) on the top of the column 300 may for example employ red or green (flashing) lights 392 to highlight that a vacuum has been applied and that the column 300 is ready for use. The column is then operational and may be used for the separation and/or purification of chemicals and/or biomolecules. On completion of the separation and/or purification process, the vacuum is released and the backing plate may be removed from the distributor plate for cleaning purposes or inspection without the need to remove many screws or bolts.

FIG. 3b is a front perspective view of the column shown in FIG. 3a but without the partial cut away or sectional view. As can be seen, externally viewed the column is very similar to the column shown in FIG. 1 and has the same component parts as described above for the prior art column. The column 300 is fabricated from strong, inert materials such as stainless steel, and is supported on legs 302 having feet 304 which may be adjustable. The column comprises a cylindrical housing or tube 306 which is also made of a strong, inert material suitable for GMP environments such as stainless steel. The tube 306 separates an adapter assembly 320 from a base assembly 310. Adjacent to the adapter assembly is a dispersion system 330 for the introduction of buffer or other mobile phase liquids or chemicals/biological molecules to be separated and/or purified. As discussed in relation to the prior art column described in FIG. 1 above, the adapter assembly 320 may be movable within the cavity 308 of the tube 306 in an operational mode to pack or compress the bed of chromatographic media used in the chromatographic separation of chemicals and biological molecules.

The significant difference in the column of FIG. 3b to the prior art column of FIG. 1 is that the distributor plate of the adapter assembly is secured to the backing plate by means of a negative pressure or vacuum (as described in FIG. 3a above) rather than by many releasable fixing means such as screws or bolts. Optionally, and in addition to this feature, the base assembly may also be designed to utilize this same method to secure the backing plate to the distributor and thus obviate the need for many fixing means such as screws or bolts.

This feature not only simplifies the design and manufacture of the adapter and backing assembly but also simplifies the workflow in setting up and cleaning the column, thus saving operator time and reducing potential errors.

The skilled person will understand that either or both the adapter assembly and the base assembly may be configured to enable securing of the distributor to the backing plate.

Whilst the present invention has been described in accordance with various aspects and preferred embodiments, it is to be understood that the scope of the invention is not considered to be limited solely thereto and that it is the Applicant's intention that all variants and equivalents thereof also fall within the scope of the appended claims.

The invention claimed is:
1. A chromatography column comprising:
a) a liquid inlet and a liquid outlet;
b) a tube connected to an adapter assembly and a base assembly to define a cavity therebetween, said adapter assembly comprising a first backing plate and a first distributor plate and said base assembly comprising a second backing plate and a second distributor plate, wherein the adapter assembly is movable within the cavity, and the first backing plate and the first distributor plate or the second backing plate and the second distributor plate have a contacting surface therebetween;

c) a seal positioned between the first backing plate and the first distributor plate or between the second backing plate and the second distributor plate, said seal defining an air pocket therebetween; wherein the seal, the air pocket, and the contacting surface are on the same horizontal plane d) the first backing plate or the second backing plate having a passage in fluid connection with said air pocket; or e) a vacuum pump configured to (i) remove the air pocket via the passage, for securing the first distributor plate to the first backing plate and the second distributor plate to the second backing plate.

2. The column of claim 1, wherein said vacuum pump is not an integral part of the column.

3. The column of claim 1, wherein the first backing plate and the second backing plate each have a passage in fluid connection with said air pocket or chamber and the vacuum pump.

4. The chromatography column of any of claim 1, wherein said seal is one or more O-rings.

5. The chromatography column of claim 1, further comprising a locating device configured to co-locate the first backing plate and the first distributor plate and the second backing plate and the second distributor plate.

* * * * *